United States Patent [19]
Kangasaho et al.

[11] Patent Number: 5,919,755
[45] Date of Patent: Jul. 6, 1999

[54] MEDICAL USE OF HEME PRODUCTS

[75] Inventors: Mauno Kangasaho; Klaus Relander, both of Turku, Finland

[73] Assignee: Leiras OY, Finland

[21] Appl. No.: 08/875,440

[22] PCT Filed: Jan. 25, 1996

[86] PCT No.: PCT/FI96/00048

§ 371 Date: Jul. 28, 1997

§ 102(e) Date: Jul. 28, 1997

[87] PCT Pub. No.: WO96/23495

PCT Pub. Date: Aug. 8, 1996

[30] Foreign Application Priority Data

Jan. 30, 1995 [FI] Finland ..................... 950389

[51] Int. Cl.⁶ ................................. A61K 31/40
[52] U.S. Cl. .................. 514/6; 514/185; 514/815
[58] Field of Search ................ 514/6, 185, 815

[56] References Cited

U.S. PATENT DOCUMENTS 4,657,902  4/1987  Kappas et al. ............ 514/185
4,692,440  9/1987  Kappas et al. .
4,699,903  10/1987  Rideout et al. .
5,008,388  4/1991  Ingberg et al. .

FOREIGN PATENT DOCUMENTS

WO 83/00287  2/1983  WIPO .

OTHER PUBLICATIONS

Medline AN 95261065. Fibach et al, May 15, 1995.
Malik, Z. and Djaldetti, M. (1980). "Cytotoxic Effect of Hemin and Protoporphyrin on Chronic Lymphocytic Leukemia Lymphocytes." *Exp. Hematol.* 8:867–879.
Timonen, T.T.T. and Kauma, H. (1992). "Therapeutic effect of heme arginate in myelddysplastic syndromes." *Eur. J. Haematol.* 49:234–238.
Volin, L. et al. (1988). "Heme Arginate Treatment for Myelodysplastic Syndromes." *Leukemia Res.* 12:423–431.
Chemical Abstracts 109:229181b (1988). "Manufacture of iron-enriched cheese for treatment of cancer".
Chemical Abstracts 111:89902f (1989). "Cytotoxic effect of hemin on L615 mouse leukemia cells".

*Primary Examiner*—Rebecca Cook
*Attorney, Agent, or Firm*—Rothwell, Figg, Ernst & Kurz, P.C.

[57] ABSTRACT

The invention is to a method for stimulating the production of fetal hemoglobin in a mammal having a hemoglobinopathy, comprising administering heme or a derivative thereof.

6 Claims, 2 Drawing Sheets

MEDICAL USE OF HEME PRODUCTS

This is a 371 of PCT/F196/WO48 filed Jan. 25, 1996.

FIELD OF THE INVENTION

The present invention relates to the use of heme or a derivative thereof for the prevention of or for the decrease of risk of mutagenesis in mammalian cells. The invention relates further to the use of heme or a derivative thereof to decrease the proportion of blasts in bone marrow in mammals and consequently to prevent the transformation of preleukemic conditions into leukemias, to prevent the disease progression in leukemias and to cure leukemias in mammals. In addition, the invention relates to the use of heme or derivatives thereof to ameliorate clinical symptoms of hemoglobinopathic conditions (e.g. μ-thalassemias and sickle cell anemias) in mammals especially via inducing production of fetal hemoglobins.

BACKGROUND OF THE INVENTION

The publications and other materials used herein to illuminate the background of the invention, and in particular, cases to provide additional details respecting the practice, are incorporated by reference.

Heme is an important endogenous substance (haem, iron protoporphyrin IX). There is no International Nonproprietary Name (DCI) for heme. The chemical state and stability of heme are influenced by the solvent and other environmental conditions.

The term "heme" is used generically here. Other terms refer to specific chemical states of heme. The Fe of heme may be either in the ferrous ($Fe^{2+}$) or ferric state ($Fe^{3+}$) and is coordinated with the 4 pyrrole nitrogens. "Hematin" is a ferric form and refers to heme dissolved in alkaline solution (heme hydroxide) or neutral solution. "Hemin" is another ferric form in which a chloride ion is coordinated to iron at the fifth or sixth position, as occurs when heme is dissolved in an aqueous solution containing HCl. Hemin is highly stable in crystalline form but is poorly soluble. When heme chloride is dissolved in alkaline solution the chloride is replaced by hydroxyl to form hematin, which is poorly stable and readily forms poorly characterized degradation products.

Heme is also stable when bound to proteins or amino acids such as arginine or lysine. Heme arginate is a product of heme and L-arginine (1). Arginine increases the aqueous solubility and stability of heme. Once heme arginate is infused into the blood stream the heme arginate dissociates and the heme moiety is quickly bound to the plasma proteins in monomeric form (1). Therefore, the formulation of heme as heme arginate augments the stability of heme for intravenous infusion and does not change its physiological utilization. Thus the discoveries presented hereinafter for heme arginate are valid also for other heme preparations. The benefit of using heme arginate instead of other presently known heme preparations is its higher stability and consequently consistent efficacy and lack of serious adverse effects known to be caused by degradation products of heme.

Lyophilized hematin (Panhematin®, Abbott) was approved by the U.S. Food and Drug Administration in 1983. Heme arginate (Normosang®, Leiras) was developed in Finland and is now marketed in several countries in Europe for treatment of acute porphyric attacks. Previously, hematin was prepared in research laboratories or hospital pharmacies, usually from outdated human blood. A preparation of heme albumin was developed in Germany.

The use of hematin (either Panhematin® or hematin prepared in research laboratories) is often complicated by adverse effects, including phlebitis at the infusion site and disturbances in hemostasis (2, 3, 4). Heme arginate seldom produces these effects and therefore is better tolerated. The side effects of Panhematin® are greatly reduced if the drug is reconstituted with human albumin in equimolar amounts (5). However, this adds considerable expense and the potential risk of administration of a protein product originating from human blood.

Heme and its derivatives have also been reported in the patent literature. The Finnish patent publication F1 68970 discloses a method for the preparation of heme arginate and heme lysinate and the use of said compounds in the treatment of porphyria. U.S. Pat. No. 5,233,034 relates to a process for the purification of hemin and to a novel hemin derivative, i.e. an 1:3-adduct of hemin and DMI and its preparation. Finnish patent application No. 841199 relates to a method for the stabilization of hematin by use of albumin.

EP 337598 discloses the use of various metalloporphyrins including hemin for the treatment of diseases caused by HIVs. WO 92/02242 describes the use of metalloporphyrins including heme and heme arginate for the treatment of retroviral infections such as AIDS.

Mutagenesis and carcinogenesis

Most cancers are initiated by genetic change. Thus cells of a given cancer can often be shown to have a shared abnormality in their DNA sequence. This does not yet prove that genetic change is an essential first step in the causation of cancer. A more solid argument is that most of the agents known to cause cancer cause genetic change and, conversely, agents that cause genetic change cause cancer. This correlation between carcinogenesis (the generation of cancer) and mutagenesis (generation of genetic change) is clear for chemical carcinogens, ionizing radiation, and viruses (6).

Mutagenesis in a hematopoietic cell may cause clonal expansion of immature hematopoietic cells (blasts) and consequently cause preleukemic conditions (like myelodysplastic syndromes) and leukemias (7). Thus the antimutagenic action of heme and its ability to decrease the proportion of blasts in the bone marrow of myelodysplastic syndromes are interrelated and may involve similar mechanisms of action.

Myelodysplastic syndromes and methods for their treatment

The myelodysplastic syndromes (MDS) are a rather heterogeneous group of acquired, multipotent stem cell disorders characterized by ineffective and dysplastic hemopoiesis resulting in symptomatic anaemia, leukopenia, and thrombocytopenia. The marrow progenitor cells show an impaired growth which is not attributable to inhibitors in the marrow. During the course of MDS the dysfunction of the marrow progresses as shown by cytogenetic analysis and precursor cell differentiation becomes more and more impaired. The clinical course is variable, ranging from a stable, mildly symptomatic disorder to one that progresses rapidly to overt acute leukaemia. Bleeding and recurrent infections are the most frequent causes of morbidity and mortality.

Myelodysplasia may be primary, without any recognizable responsible factor, or secondary to exposure to ionising radiation, alkylating agents or some organic solvents (7). In the material from the district of Düsseldorf approximately 5% of the patients with MDS had the secondary type of this disease (8).

In 1982 the FAB group proposed a clinical classification system for MDS (9) which has been generally adopted (Table 1). Several studies have shown that FAB classification system has also a prognostic significance (Table 1) (10). Especially the median survival time is affected by the proportion of blasts in bone marrow.

TABLE 1

FAB classification of the myelodysplastic syndrome ( 9 ). Median survival is presented as shown by Kouides and Bennett (11).

| Subtype | Blood | Bone marrow | Median survival (Months) |
|---|---|---|---|
| Refractory anemia (RA) | Blasts < 1% | Blasts < 5% Sideroblasts < 15% | 32–50 |
| Refractory anemia with ring sideroblasts (RARS) | Blasts < 1% | Blasts < 5% Sideroblasts > 15% | 45–76 |
| Chronic myelomonocytic leukaemia (CMML) | Blasts < 5% Monocytes > 1 × 10⁹/l | Blasts < 20% Promonocytes | 11–22 |
| Refractory anemia with excess of blasts (RAEB) | Blasts < 5% | Blasts 5–20% | 11–19 |
| Refractory anemia with excess of blasts in transformation (RAEB-t) | Blasts > 5% or Auer rods | Blasts 21–30% or Auer rods | 3–11 |

Proposed therapeutic modalities for MDS are extremely divergent including supportive measures, corticosteroids, anabolic steroids, differentiating agents, biologic response modifiers, haematopoietic growth factors, heme arginate, low-dose chemotherapy, intensive chemotherapy, and high dose chemo-radiotherapy with bone marrow transplantation (12).

Efficacy of heme arginate in myelodysplastic syndromes

Heme arginate has been used in treatment of myelodysplastic syndromes by two independent groups of investigators.

Volin et al. (13, 14) gave heme arginate to 26 patients with myelodysplastic syndrome of the subgroups RA, RARS, RAEB, or RAEBt at the dose 2–3 mg hemin/kg in most cases first on four consecutive days and after that once a week for 8 to 12 weeks. Six of the patients showed improvement in cytopenias during the therapy and three of them had long-lasting (>11, >12, and 25 months) good response with normal or close to normal blood cell counts.

Timonen and Kauma (15) treated 14 patients with myelodysplastic syndrome of the subtypes RA, RARS, or RAEB at the dose 3 mg hemin/kg on four consecutive days at two weeks intervals mostly for six treatment cycles. Three of the patients had long-lasting (5, 26, and >41 months) improvement in hemoglobin values and/or platelet counts.

Hemoglobinopathies

Each molecule of hemoglobin consists of four polypeptide (globin) chains and four molecules of heme. There are four different types of the globin chains ($\alpha$, $\beta$, $\delta$, and $\gamma$) constituting a hemoglobin molecule in combinations of two plus two. In an adult human the major types of hemoglobin molecules are Hb-A$_1$ ($\alpha_2$, $\beta_2$) and Hb-A$_2$ ($\alpha_2$, $\beta_2$). During the fetal period and during the first year after birth the fetal hemoglobin type Hb-F ($\alpha_2$, $\gamma_2$) is also present. Pathological inherited abnormalities in the structure of hemoglobins are called with the general name hemoglobinopathies (16).

More than 100 different abnormal hemoglobins are known, each produced by a mutation affecting one type of polypeptide chain. In sickle cell anemia e.g. the $\beta$-globin gene is mutated in a way that one amino acid residue is changed (glu$_6$- val$_6$) in the globin chain. However, this small change affects the function of the hemoglogin and red blood cells to cause a severe disease with hemolytic anemia (16).

The thalassemias are a group of anemias in which the production of $\alpha$ chain, $\beta$ chain or $\beta$ and $\gamma$ chains is greatly reduced or absent. The severity of thalassemias depend on the subtype and whether the abnormal gene is present with heterozygote or homozygote expression. The $\beta$-thalassemia e.g. is often expressed as severe microcytic anemia (16).

An increase in Hb-F in patients with $\beta$-thalassemias (e.g. sickle cell anemia, $\beta$-thalassemia) may ameliorate the clinical symptoms of the disease. In sickle cell anemia, not only do HbF-containing cells have lower concentration of sickle hemoglobin (Hb-S), but Hb-F directly inhibits polymerization of Hb-S, thus accounting for the lower propensity of such cells to form intracellular polymer and undergo sickling. In $\beta$-thalassemia, the elevated $\gamma$ chain should partially compensate for the deficiency in $\beta$ chains relative to a chains. Recently, several pharmacological agents, e.g. hydroxyurea and 5-azacytidine, have been used to stimulate Hb-F synthesis in patients with hemoglobinopathies (17, 18, 19, 20).

SUMMARY OF THE INVENTION

The present invention relates to the use of heme or a derivative thereof for the preparation of a pharmaceutical composition useful for the prevention of mutagenesis or for the decrease of the risk of mutagenesis in mammalian cells, especially in mammalian hematopoietic cells.

The invention relates further to the use of heme or a derivative thereof for the preparation of a pharmaceutical composition useful to decrease the proportion of blasts in bone marrow in mammals. According to one aspect of the invention, said pharmaceutical composition is intended for use in the treatment of myelodysplastic syndromes in order to slow down or prevent progression of the disease into more malignant MDS subtypes (RAEB, RAEB-t) or into leukemia. According to another aspect said pharmaceutical composition is intended for use in the treatment of other preleukemic diseases or states in order to slow down or prevent progression of the disease into more malignant forms of the disease or into leukemia. According to still another aspect said pharmaceutical composition is intended for use in the treatment of leukemias in order to slow down or prevent disease progression or to transform the disease into preleukemic or non-leukemic state.

The invention additionally relates to the use of heme or a derivative thereof for the preparation of a pharmaceutical composition useful for inducing production of fetal hemoglobin (Hb-F) in mammalian erythroid cells and causing by this or other mechanism(s) amelioration of clinical symptoms of hemoglobinopathies (especially sickle cell anemias and $\beta$-thalassemia).

The pharmaceutical preparation of this invention may further contain or it can be used concomitantly with another pharmaceutical preparation containing an inhibitor of heme catabolism, a cytostatic agent, a retinoid or other differentiation inducing agent, a cytokine, a biological growth factor, an agent known to induce production of fetal hemoglobin or the like. The heme catabolism inhibitor may for example be a tin or zinc protoporphyrin or a tin or zinc mesoporphyrin.

The "heme or a derivative thereof" shall include heme, hematin, hemin, amino acid addition salts of heme, and heme albumin (heme reversibly bound to albumin) as well as biochemical precursors of heme such as protoporphyrin IX, amino acid addition salts of said precursors and their reversible complexes with albumin. Particularly preferable derivatives are heme arginate and heme lysinate.

DETAILED DESCRIPTION OF THE INVENTION

Figure 1:
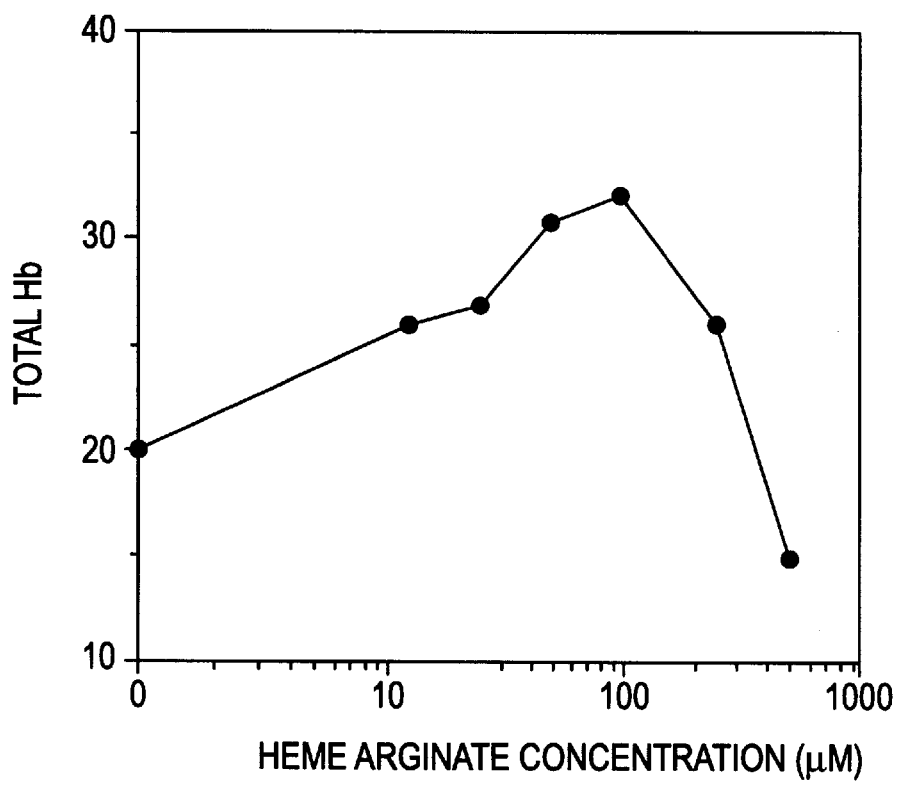
FIG. 1 shows the effect of hemi arginate on total hemoglobin production by cultured human erythroid precursors. Cells grown in phase II in the presence of the indicated concentrations of heme arginate, were harvested on day 13 and their hemoglobin quantitated.

It was discovered that a heme preparation (heme arginate) was able to decrease incidence of mutagenesis (mouse micronucleus test) in the mouse in vivo (Table 2). In the mouse the antimutagenic effect was demonstrated at rather high dose level of 36 mg/kg. In humans the active dose level can, however, be much lower (even 10-times lower) because the elimination rate is slower in humans (AUC 998 $\mu$g/ml/h) than in rodents (AUC in the rat 64 $\mu$g/ml/h). The both AUC values were observed after the intravenous dose of 3 mg/kg (21 and Kangasaho, unpublished information).

Thus heme preparations can be used for decreasing incidence of mutagenesis in patients treated with known mutagenic therapies like cytostatics and/or radiotherapy. In addition heme preparations can be used in prevention of mutagenesis or progress of mutagenic development in persons exposed to mutagenic chemicals or radiation in accidents or via environmental or occupational circumstances.

It was also discovered that a heme preparation (heme arginate) was able to decrease proportion of blasts in bone marrow of some patients with myelodysplastic syndromes (MDS). It is known that heme arginate is clinically effective in part of MDS patients by increasing the blood cell counts. However, there has been fear that the use of heme therapy (13, 14, 15) like the use of other hematopoietic growth factors in MDS patients may increase the risk of disease progression into leukemias via enhancing the proportion of blasts. Surprisingly it was noticed in a clinical study that heme arginate was able to decrease proportion of blasts (blasts and myeloblasts) in bone marrow of some MDS patients (Table 3). This finding is clinically significant because the proportion of blasts in the bone marrow is strongly correlated into the expected survival time of the patient (Table 1) and the natural course of MDS varies from a relatively static to aggressive progression i.e. spontaneus remission can not be expected (14). In the published studies MDS progression was seen in 4/26 patients (13) and in 4/14 patients (15) which is considered to be normal in these patients. In the latter study (15) decrease of blasts in 1/14 patient was reported but considered to be an occasional event. In the data presented here a clear decrease was reported in 5/21 patients (Table 3) with a smaller decrease in 12/21, no effect in 1/21 and slight increase in 3/21 patients (Table 4). Thus some decrease was seen totally in 17/21 patients. However, the clinically significant bone marrow blast decreasing activity of heme seems to be limited to a patient subpopulation.

Thus treatment with heme preparations by decreasing the proportion of blasts in bone marrow in a patient subpopulation can prevent transformation of "milder" subtypes of the MDS into the more malignant subtypes (RAEB, RAEB-t) and further into leukemia. Because increase in the proportion of blasts in bone marrow is the most critical factor in development of leukemia, heme preparations can be active also in other preleukemic conditions than the MDS.

In one of the patients the proportion of blasts (blasts+ myeloblasts) in bone marrow was 30% before start of the treatment with heme arginate and it decreased into 10% after the treatment. Because 30% proportion of blasts in bone marrow is the limit value between MDS (RAEB-t) and acute leukemia (Table 1) it can be assumed that treatment with heme preparations can be effective also in leukemias (slowing down or prevention of disease progression or even transformation of leukemia back into preleukemic or non-leukemic state) and not only in preleukemic diseases like the MDS.

Figure 2:
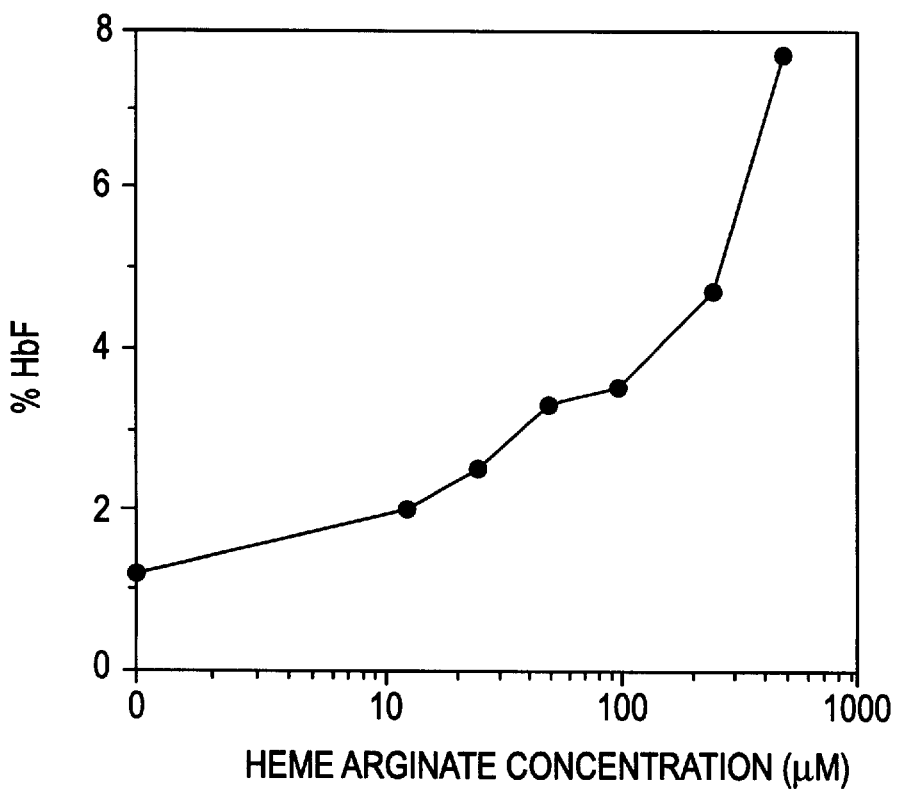
FIG. 2 shows the effect of heme arginate concentration on fetal hemoglobin (Hb-F) production by cultured human erythroid precursors. Cells grown in phase II in the presence of the indicated concentrations of heme arginate, were harvested on day 13 and their hemoglobin chromatographed and quantitated.
Figure 3:
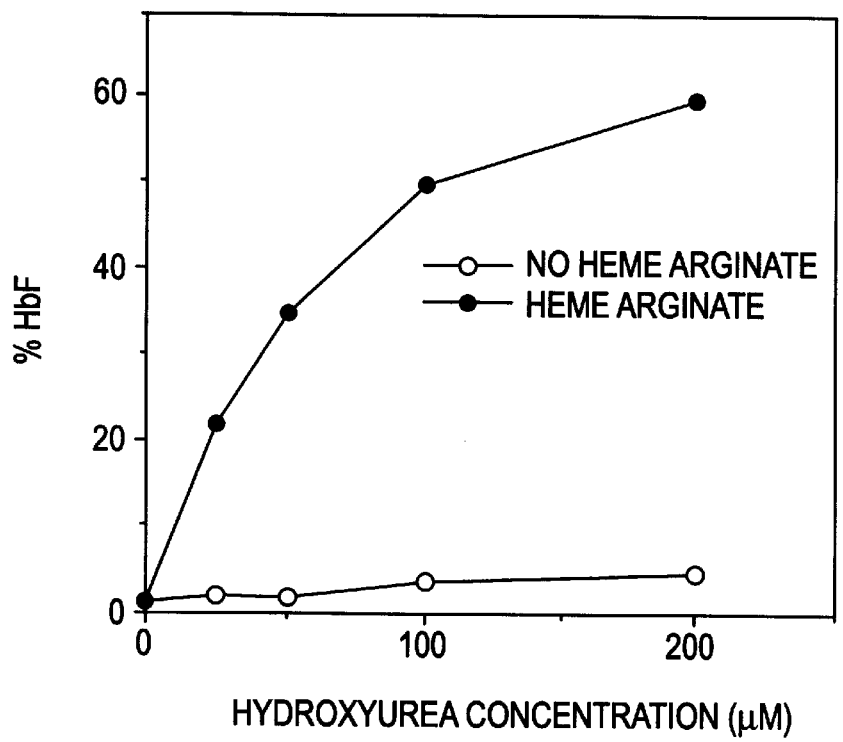
FIG. 3 shows the effect of hydroxyurea (25–200 $\mu$M) with or without hemi arginate (100 $\mu$M) on fetal hemoglobin (Hb-F) production by cultured human erythroid precursors. Cells grown in phase II in the absence or presence of heme arginate from day 0 and with the indicated concentrations of hydroxyurea from day 5, were harvested on day 13 and their hemoglobin chromatographed and quantitated.
Figure 4:
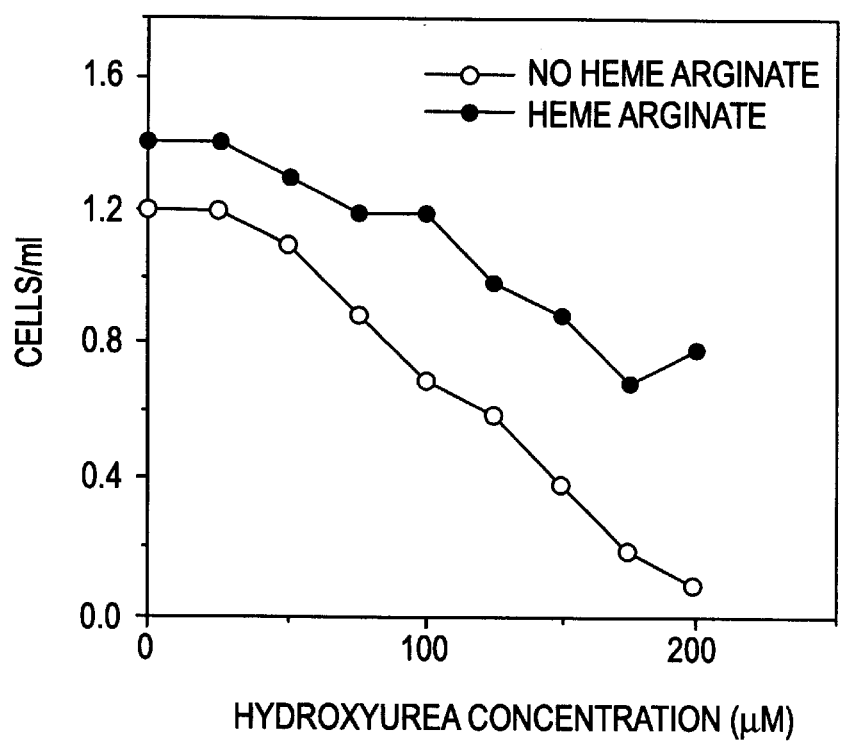
FIG. 4 shows the effect of hydroxyurea (25–200 $\mu$M) with or without hemi arginate (100 $\mu$M) on cell proliferation by cultured human erythroid precursors. Cells grown in phase II in the absence or presence of heme arginate from day 0 and with the indicated concentrations of hydroxyurea from day 5, were harvested on day 13 and their hemoglobin chromatographed and quantitated.

It was also discovered that heme arginate can affect the globin chain expression in erythroid precursor cells originating from patients with hemoglobinopathies ($\beta$-thalassemias, sickle cell anemia). Heme arginate increases the amount of total hemoglobin (FIG. 1) produced by these cells and increases the proportion of fetal hemoglobin (FIG. 2). It is especially surprising how strongly the effect of heme arginate on the proportion of fetal hemoglobin was potentiated by the presence of hydroxyurea (FIG. 3).

The ability of heme arginate alone or in combination with hydroxyurea (or other agents) to induce fetal hemoglobin production is of considerable clinical importance. An increase in fetal hemoglobin in patients with hemoglobinopathies (like $\beta$-thalassemia and sickle cell disease) may ameliorate the clinical symptoms of the disease.

In addition to heme preparations also other tretments can be used concomitantly to enhance the therapeutic potential of heme. Such concomitant treatments can be e.g. inhibitors of heme catabolism (like tin or zink-protoporphyrins, tin or zink-mesoporphyrins etc.) or cytostatics (especially at low dose) etc., retinoids or other differentiation inducing agents, cytokines, biological growth factors etc. and in the case of hemoglobinopathies hydroxyurea or other pharmacological agents known to induce production of fetal hemoglobin.

Methods

1. Mouse micronucleus assay

In mitotic cells in which chromosomal damage has been caused acentric fragments of the chromosomes do not separate at the anaphase stage of cell division. After telophase these fragments may not be included in the nuclei of the daughter cells and hence will form single or multiple micronuclei (Howell-Jolly bodies) in the cytoplasma of these cells. Micronuclei are seen in a variety of cells, but erythrocytes are chosen for examination since micronuclei are easily detected in this cell type.

A few hours after the last mitosis is completed, erythroblasts expel their nucleus. Young erythrocytes stain blue with Giemsa due to the presence of ribonucleic acid, which gradually disappears so that more mature erythrocytes stain pink with Giemsa. The young blue-staining cells are known as polychromatic erythrocytes and micronuclei are readily detected in this cell type.

The test animals were specific pathogen free CD-1 outbred mice of Swiss origin weighing between 22 and 24 grams and approximately 40 days old during the study. The mice were acclimatized for four days and after that dosed by intravenous injection with a volume of 10 ml/kg body weight either with saline solution (vehicle control) or with heme arginate solution at the dose 36 mg hemin/kg body weight. Five male and five female mice were sacrificed by cervical dislocation 24, 48, and 72 hours after dosing. A direct bone marrow smear was made from femur onto a slide containing a drop of calf serum. The smears were fixed in methanol, air dried, and stained for 10 minutes in 10% Giemsa solution. The stained smears were examined (under code) by light microscopy to determine the incidence of micronucleated cells per 1000 polychromatic erythrocytes per animal.

2. Proportion of blasts in the bone marrow of myelodysplastic patients

In a clinical study patients with myelodysplastic syndromes were treated with intravenous infusions of heme arginate at the dose level 3 mg hemin/kg. The infusions were given first on four consecutive days and after that once a week for eleven weeks. Thus totally 15 infusions were given to each patient.

Bone marrow sample was collected from each patient before start of the heme arginate infusions and one week after the last infusion. Proportion of blasts and myeloblasts were determined in the bone marrow samples by using standard hematological laboratory procedures. The definition of "a blast" as used in the classification of myelodysplastic syndromes includes both blasts and myeloblasts (9).

3. Induction of production of fetal hemoglobin in vitro

Peripheral blood mononuclear cells obtained from normal volunteers and either sickle cell anemia or β-thalassemia patients were isolated by centrifugation on a gradient of Ficoll-Hypaque and seeded at a density of $5 \times 10^6$ cells/ml in alpha-minimal essential medium supplemented with 10% fetal calf serum (FCS), 1 μg/ml cyclosporin A, and 10% conditioned medium collected from cultures of the 5637 bladder-carcinoma cell line. The cultures were incubated at +37° C. in an atmosphere of 5% $CO_2$ in air with extra humidity.

Following 7-day incubation in this phase I culture, the non-adherent cells were harvested, washed, and recultured in fresh medium composed of alpha-medium, 30% FCS, 1% deionized bovine serum albumin, $1 \times 10^{-5}$ M β-mercaptoethanol, 1.5 mM glutamine, $1 \times 10^{-6}$ M dexamethasone, and 1 U/ml human recombinant erythropoietin. Hemoglobin containing cells were determined by using the benzidine-HCl procedure.

The effect of heme arginate on fetal hemoglobin (Hb-F) production was determined by growing human erythroid precursors in the second phase of the above described liquide cell culture in the presence of 1 U/ml erythropoietin and different concentrations of heme arginate. The combination effect of heme arginate and hydroxyurea was investigated with 100 μM heme arginate added on day 0 and various concentrations of hydroxyurea added on day 5. Cells were harvested on day 13 and lysed, and their total hemoglobin and Hb-F content was analyzed by cation-exchange HPLC.

Results

The results are presented in the Tables 2, 3 and 4 and in FIGS. 1 to 4 enclosed.

TABLE 2

Activity of heme arginate in the mouse micronucleus test in vivo.

| Time of killing the mice after dosing | Compound | Dosage | Incidence*[)] |
|---|---|---|---|
| 24 hours | Vehicle control | — | 1.2‰ |
|  | Heme arginate | 36 mg/kg i.v. | 1.1‰ |
| 48 hours | Vehicle control | — | 1.0‰ |
|  | Heme arginate | 36 mg/kg i.v. | 0.5‰ |
| 72 hours | Vehicle control | — | 1.0‰ |
|  | Heme arginate | 36 mg/kg i.v. | 0.4‰ |

*[)]Incidence: Number of micronucleated polychromatic erythrocytes observed in bone marrow smears per 1000 polychromatic erythrocytes examined.

TABLE 3

Effect of heme arginate treatment in blasts the proportion of blasts in bone marrow of some patients with myelodysplastic syndromes (RAEB or RAEB-t). For classification of the myelodysplastic syndromes see Table 1.

| Patient | Blasts in bone marrow | | Myeloblasts in bone marrow | | Sum of blasts and myeloblasts in bone marrow | | Myelodysplastic syndrome subtype | |
|---|---|---|---|---|---|---|---|---|
|  | Before | After | Before | After | Before | After | Before | After |
| 1 | 4% | 0% | 6% | 4% | 10% | 4% | RAEB | RARS |
| 2 | 3% | 0% | 8% | 4% | 11% | 4% | RAEB | RARS |
| 3 | 6% | 1% | 4% | 3% | 10% | 4% | RAEB | RARS |
| 4 | 15% | 4% | 3% | 4% | 18% | 8% | RAEB | RAEB |
| 5 | 10% | 6% | 20% | 4% | 30% | 10% | RAEB-t | RAEB |

TABLE 4

Effect of heme arginate treatement in blasts. The proportion of blasts in bone marrow of myelodysplastic syndrome (RARS or RAEB) patients who were not considered as good responders. For classification of the myelodysplastic syndrome see Table 1.

| Patient | Blasts in bone marrow | | Myeloblasts in bone marrow | | Sum of blasts and myeloblasts in bone marrow | | Myelodysplastic syndrome subtype | |
|---|---|---|---|---|---|---|---|---|
|  | Before | After | Before | After | Before | After | Before | After |
| 6 | 5 | 5 | 4 | 3 | 9 | 8 | RAEB | RAEB |
| 7 | 5 | 5 | 4 | 3 | 9 | 8 | RAEB | RAEB |
| 8 | 8 | 8 | 4 | 3 | 12 | 11 | RAEB | RAEB |
| 9 | 2 | 0 | 2 | 2 | 4 | 2 | RARS | RARS |
| 10 | 3 | 2 | 2 | 1 | 5 | 3 | RARS | RARS |
| 11 | 3 | 0 | 4 | 7 | 7 | 7 | RAEB | RAEB |
| 12 | 1 | 2 | 8 | 6 | 9 | 8 | RAEB | RAEB |
| 13 | 5 | 3 | 9 | 10 | 14 | 13 | RAEB | RAEB |
| 14 | 4 | 1 | 3 | 3 | 7 | 4 | RAEB | RARS |
| 15 | 3 | 3 | 10 | 9 | 13 | 12 | RAEB | RAEB |
| 16 | 0 | 1 | 5 | 3 | 5 | 4 | RAEB | RARS |
| 17 | 0 | 3 | 3 | 3 | 3 | 6 | RARS | RAEB |
| 18 | 1 | 1 | 4 | 5 | 5 | 6 | RAEB | RAEB |
| 19 | 2 | 1 | 1 | 0 | 3 | 1 | RARS | RARS |
| 20 | 0 | 2 | 1 | 2 | 1 | 4 | RARS | RARS |
| 21 | 5 | 4 | 5 | 5 | 10 | 9 | RAEB | RAEB |

For the purpose of the invention heme or its derivative can be administered by various routes. The suitable administration forms includes parenteral injections and implants including intravenous, intramuscular, intradermal and subcutanous injections; oral formulations and suppositories.

The required dose of heme or its derivative will vary with the particular condition being treated, the severity of the condition, the duration of the treatment, the administration route, and the specific heme compound, the specific pharmaceutical composition, or the specific combination of concomitant treatments being employed. Possible use of heme catalysis inhibitors (as part of the pharmaceutical composition or concomitant use) decreases the preferred dose of heme or derivatives thereof. For intravenous administration the preferrable daily doses of heme or derivatives thereof range from 0.1 to 15 mg/kg calculated as hemin equivalents. For other administration routes (p.o., s.c., i.p., i.m.) the preferrable daily dose may vary depending on each specific pharmaceutical composition of heme or a derivative thereof. However, the preferrable daily dose will be one resulting in systemic daily release ("bioavailable dose") of 0.1–15 mg/kg calculated as hemin equivalents.

It will be appreciated that the methods of the present invention can be incorporated in the form of a variety of embodiments, only a few of which are disclosed herein. It will be apparent for the person skilled in the art that other embodiments exist and do not depart from the spirit of the invention. Thus, the described embodiments are illustrative and should not be construed as restrictive.

References

1. Sievers G, Hakli H, Luhtala J, Tenhunen R. Optical and EPR spectroscopy studies on haem arginate, a new compound used for treatment of porphyria. Chem Biol Interactions 1987;63: 105–14.

2. Goetsch C A, Bissell D M. Instability of hematin used in the treatment of acute hepatic porphyria. N Engl J Med 1986; 315:235–8.

3. McColl K E L, Moore M R, Thompson G G, Goldberg A. Treatment with haematin in acute hepatic porphyria. Quart J Med 1981;198: 161–74.

4. Simionatto C S, Cabel R, Jones R L, Galbraith R A. Thrombophlebitis and disturbed hemostasis following administration of intravenous hematin in normal volunteers. Am J Med 1988;85:538–40.

5. Bonkovsky H L, Healey B S, Lourie A N, Gerron G G. Intravenous heme-albumin in acute intermittent porphyria: evidence for repletion of hepatic hemoproteins and regulatory heme pools. Am J Gastroenterol 1991;86:1050–6.

6. Alberts B, Bray D, Lewis J, Raff M, Roberts K, Watson J D. Molecular biology of the cell. 2nd ed. New York: Garland Publishing, 1989.

7. Levine E G, Bloomfield C D. Leukemias and myelodysplastic syndromes secondary to drug, radiation, and environmental exposure. Semin Oncol 1992;19:47–84.

8. Aul C, Gattermann N, Runde V, Heyll A, Germing U, Schneider W. How frequent are myelodysplastic syndromes. Ann Hematol 1992;65 suppl:A32.

9. Bennett J M, Catovsky D, Daniel M T, Flandrin G, Galton D A G, Gralnick H R, Sultan C. The French-American-British (FAB) Cooperative Group. Proposals for the classification of the myelodysplastic syndromes. Br J Haematol 1982;51:189–99.

10. Goasguen J E, Bennett J M. Classification and morphologic features of the myelodysplastic syndromes. Semin Oncol 1992;19:4–13.

11. Kouides P A, Bennett J H. Morphology and classification of myelodysplastic syndromes. Hematol Oncol Clin North Amer 1992;6:485–99.

12. Mittelman M. The myelodysplastic syndromes-1990. Israel J Med Sci 1990;26: 468–78.

13. Volin L, Ruutu T, Knuutila S, Tenhunen R. Heme arginate treatment for myelodysplastic syndromes. Leukemia Res 1988;12:423–31.

14. Volin L. Haem arginate in myelodysplastic syndromes and hereditary siderblastic anaemias. University of Helsinki, Academic Dissertation in Medicine, 1989.

15. Timonen T T T, Kauma H. Therapeutic effect of heme arginate in myelodysplastic syndromes. Eur J Haematol 1992;49:234–8.

16. Woolf L I. Hemoglobinopathies. In: Diem K, Lentner C, editors. Scientific tables. 7th Ed. Basle: Ciba-Geigy: 446–448.

17. Noguchi C T, Schechter A N. The intracellular polymerization of sickle hemoglobin and its relevance to sickle cell disease. Blood 1981;58:1057–68.

18. Schechter A N, Noguchi C T, Rodgers G P. Sickle cell anemia. In: Stamatoyannaopoulos G, Nienhuis A W, Leder P, Majerus P W, editors. Molecular basis of blood diseases. Philadelphia: Saunders, 1987:179–218.

19. Ley T J , DeSimone J, Noguchi C T, Turner P R, Schechter A N, Heller P, Nienhuis AW. 5-azacytidine increases γ-globin synthesis and reduces the proportion of dense cells in patients with sickle cell anemia. Blood 1983:62:370–80.

20. Charache S, Dover G J, Moore R D, Eckert S, Ballas S K, Koshy M, Milner P F A, Orringer E P, Phillips G Jr, Platt O S, Thomas G H. Hydroxyurea: Effects on hemoglobin F production in patients with sickle cell anemia. Blood 1992:73:2555–65.

21. Tokola O, Tenhunen R, Volin L, Mustajoki P. Pharmacokinetics of intravenously administered haem arginate. Br J Clin Pharmacol 1986;22:331–5.

We claim:

1. A method for stimulating the production of fetal hemoglobin in a mammal having a hemoglobinopathy which comprises administering to a mammal in need thereof an effective amount of a heme or derivative thereof and a pharmaceutically acceptable carrier, wherein said derivative is selected from the group consisting hematin, hemin, an amino acid addition salt of heme, heme albumin, a biochemical precursor of heme, an amino acid addition salt of said precursor and a reversible complex of said precursor with albumin.

2. The method of claim 1 wherein said hemoglobinopathy is sickle cell anemia or β-thalassemia.

3. The method of claim 1 wherein the heme derivative is heme reversibly bound to albumin or an amino acid addition salt of heme.

4. The method of claim 2 wherein the heme derivative is heme arginate.

5. The method of claim 1 which further comprises administering an inhibitor of heme catabolism, a cytostatic agent, a retinoid or other differentiation-inducing agent, a cytokine, a biological growth favor, an agent which induces production of fetal hemoglobin or a mixture thereof.

6. The method of claim 5 wherein the agent administered is an inhibitor of heme catabolism selected from the group consisting of tin and zinc mesoporphyrin.

* * * * *